United States Patent [19]

Failli et al.

[11] 3,979,380
[45] Sept. 7, 1976

[54] DERIVATIVES OF IMIDAZOLIDIN-2-ONES AND -2-THIONES

[75] Inventors: Amedeo Failli, Montreal; Manfred Gotz, Hudson, both of Canada

[73] Assignee: American Home Products Corporation, New York, N.Y.

[22] Filed: June 9, 1975

[21] Appl. No.: 585,019

Related U.S. Application Data

[62] Division of Ser. No. 301,413, Oct. 27, 1972, Pat. No. 3,904,629, which is a division of Ser. No. 55,952, July 17, 1970, Pat. No. 3,707,472.

[52] U.S. Cl. .......................... 260/239.7; 260/239 B; 260/247.1 M; 260/247.2 A; 260/247.5 F; 260/268 BC; 260/293.66; 260/293.87; 260/268 N; 260/309.7; 260/306.8 R; 260/566 B; 424/273; 424/267; 427/250
[51] Int. Cl.² ............... C07D 401/04; C07D 403/04
[58] Field of Search ...................... 260/293.7, 309.7

[56] References Cited
UNITED STATES PATENTS

| | | | |
|---|---|---|---|
| 1,915,334 | 6/1933 | Salzberg et al. | 260/293.51 |
| 2,075,359 | 3/1937 | Salzberg et al. | 260/584 |
| 2,362,614 | 11/1944 | Calva | 260/253 |
| 3,115,499 | 12/1963 | Michels | 260/309.7 |

FOREIGN PATENTS OR APPLICATIONS

942,195  11/1963  United Kingdom ............. 260/309.7

OTHER PUBLICATIONS

Chemical Abstracts vol. 65 cols 8893–94 (1966) Abstracting Lempert et al.
Chemical Abstracts vol. 71 col 12470 (1962) Abstracting Mckay et al.
UGI et al. I "Liebigs Amn. Chem." vol. 666 pp. 54–61 (1963).
UGI et al. II "Angew. Chem." Internat. Ed. vol. 1 pp. 8–21 (1962).

*Primary Examiner*—Natalie Trousof
*Assistant Examiner*—Robert T. Bond

[57] ABSTRACT

There are disclosed herein derivatives of imidazolidin-2-ones and -2-thiones of the formula I

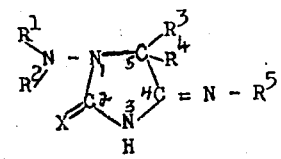

and their acid addition salts with pharmacologically acceptable acids, in which $R^1$ is hydrogen or lower alkyl; $R^2$ is lower alkyl, nitrothiazolyl, or nitrofuryl; or $R^1$ and $R^2$ together with the nitrogen to which they are attached are a heterocyclic group containing 4-6 carbon atoms, or 4 carbon atoms and an additional nitrogen atom which may optionally be substituted with a lower alkyl group, or 4 carbon atoms and an oxygen atom, $R^3$ is hydrogen or lower alkyl; $R^4$ is lower alkyl or aralkyl, or $R^3$ and $R^4$ together with the carbon atom 5 of the imidazolidine ring to which they are attached are a carbocyclic ring containing 5-6 carbon atoms attached in spiro fashion to said imidazolidine ring; $R^5$ is lower alkyl or cycloalkyl containing from 5-6 carbon atoms; and X is an oxygen or a sulfur atom. The compounds of this invention possess positive inotropic activity and are useful as cardiac stimulants.

4 Claims, No Drawings

DERIVATIVES OF IMIDAZOLIDIN-2-ONES AND -2-THIONES

RELATED U.S. APPLICATION DATA

This application is a division of Ser. No. 301,413, filed Oct. 27, 1972, now U.S. Pat. No. 3,904,629, which, in turn, is a division of Ser. No. 55,952, filed July 17, 1970, now U.S. Pat. No. 3,707,472.

BACKGROUND OF THE INVENTION

This invention relates to derivatives of imidazolidin-2-ones and -2-thiones of the formula I

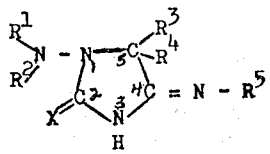

and to their acid addition salts with pharmacologically acceptable acids, in which $R^1$ is hydrogen or lower alkyl; $R^2$ is lower alkyl, nitrothiazolyl, or nitrofuryl; or $R^1$ and $R^2$ together with the nitrogen to which they are attached are a heterocyclic group containing 4-6 carbon atoms, or 4 carbon atoms and an additional nitrogen atom which may optionally be substituted with a lower alkyl group, or 4 carbon atoms and an oxygen atom, for example a piperidino, azepino, $N^4$-methylpiperazino, or a morpholino group; $R^3$ is hydrogen or lower alkyl; $R^4$ is lower alkyl or aralkyl, for example benzyl or α-methylbenzyl; or $R^3$ and $R^4$ together with the carbon atom 5 of the imidazolidine ring to which they are attached are a carbocyclic ring containing 5-6 carbon atoms attached in spiro fashion to said imidazolidine ring; $R^5$ is lower alkyl or cycloalkyl containing from 5-6 carbon atoms; and X is an oxygen or a sulfur atom. The compounds of this invention possess positive inotropic activity and are useful as cardiac stimulants, especially in the treatment of cardiac insufficiency, of shock, and of conditions associated with low cardiac output.

Compounds which may be considered as being somewhat related to the compounds of this invention of formula I, but which differ principally in having $R^1$ representing an acyl group, such as the formyl, benzoyl, or benzenesulfonyl group, with $R^2$ being hydrogen, have been described by I. Ugi in Angew. Chemie, Int. Ed., Vol. 1, p. 8 (1962), in particular pp. 18-19, and by Ugi et al. in Liebig's Ann. Chem. Vol. 666, p. 54 (1963). However, those latter compounds differ significantly from the compounds of this invention in possessing a non-basic, essentially neutral acylamino (amide) function attached to position 1 of the imidazolidine ring, while the compounds of this invention have in that same position a secondary or tertiary substituted amino group or a nitrogen-containing heterocyclic group attached to position 1 through its tertiary nitrogen atom. The fundamental differences in chemical and physical properties between an acylamino (amide) function, such as present in position 1 of the compounds described by Ugi et al., and a secondary or tertiary amino function as present in position 1 of the compounds of this invention are well known and fully recognized in the art. For example, the acylamino (amide) function is essentially neutral, while in contradistinction thereto the secondary or tertiary amino group in position 1 of the compounds of this invention is basic in nature. Moreover, the compounds described by Ugi et al., do not possess the pharmacological properties of the compounds of this invention, nor is there any suggestion to be found in the literature that they might perhaps possess cardiac stimulating activities.

SUMMARY OF THE INVENTION

The compounds of this invention of formula I are conveniently prepared in the following manner.

A substituted hydrazine of the formula II in which $R^1$ and $R^2$ are as defined in the first instance is condensed with a carbonyl compound of the formula III in which $R^3$ and $R^4$ are as defined in the first instance to yield the corresponding hydrazone of formula IV in which $R^1$, $R^2$, $R^3$ and $R^4$ are as defined above. Said last-named hydrazone is treated with an isonitrile of the formula $R^5NC$ in which $R^5$ is as defined in the first instance, in the presence of an acid of the formula HCNX in which X is as defined in the first instance, to yield the corresponding compound of formula I which may, in turn, be treated with a pharmacologically acceptable acid to obtain the corresponding acid addition salt. The following formulae will illustrate this invention.

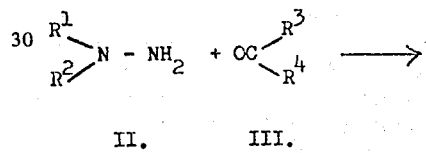

II.     III.

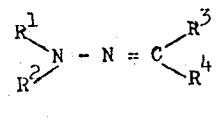

IV.

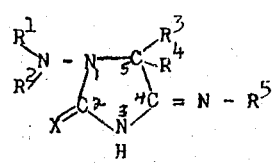

The compounds of this invention of formula I and their acid addition salts with pharmacologically acceptable acids, which are pharmacologically equivalent to the compounds themselves, possess valuable pharmacological properties. More particularly, these compounds, in standard pharmacological tests, for example in a procedure similar to that described by S. Garb, M. Penna, and A. Ganz, Amer. J. Physiol., 185 (2), p. 332 (1956), for the testing of agents possessing positive inotropic activity have exhibited such activity and are useful as cardiac stimulants in the treatment of cardiac insufficiency, of shock, and of conditions associated with low cardiac output.

When the compounds of this invention are employed as cardiac stimulants in warm-blooded animals, e.g. in rats, alone or in combination with pharmacologically acceptable carriers, the dosage of the compounds and the proportion of carriers is determined by the solubility and chemical nature of the compound, by the chosen route of administration and by standard biological practice. For example, the compounds may be administered orally in solid form containing such excipients as starch, lactose, certain types of clay, lubricants such as magnesium stearate, and similar ingredients. They may also be administered orally in the form of solutions, or they may be injected parenterally. For parenteral administration the compounds of this invention may be administered in the form of sterile solutions containing other solutes, for example, sodium chloride or glucose to make the solution isotonic.

The dosage of the compounds of this invention will vary with the form of administration and the particular compound chosen, as well as with the particular host under treatment. Generally, treatment is initiated with small dosages substantially less than the optimum dose of the compound. Thereafter the dosage is increased by small increments until the optimum effect under the circumstances is reached.

In general, the compounds of this invention are most desirably administered at a concentration dosage level which will generally afford effective results without causing any harmful side effects, and preferably at a level that is in a range of from about 5 mg to about 100 mg per kilo body weight per day, although certain variations will occur as noted above. However, a dosage level in which the range is about 10 mg to about 50 mg per kilo body weight per day is most desirably employed in order to achieve effective results.

DETAILED DESCRIPTION OF THE INVENTION

More specifically, a substituted hydrazine of the formula II, for example an N,N-di(lower alkyl)hydrazine, N-aminopiperidine, N-aminoazepine, or $N^1$-amino-$N^4$-methylpiperazine is condensed with a carbonyl compound of the formula III, for example an aldehyde or a ketone of the formula $R^3COR^4$ in which $R^3$ and $R^4$ are as defined in the first instance, or a cyclic ketone such as cyclopentanone or cyclohexanone, to yield the corresponding hydrazone of the formula IV. Said condensation is preferably carried out at an elevated temperature, or at near the reflux temperature of the mixture, in an anhydrous, water-immiscible hydrocarbon solvent, with concomitant physical removal of water as it is being formed, e.g. by means of a Dean-Stark water separator. Evaporation of the solvent and purification of the residue, for example by distillation or crystallization, yields the corresponding hydrazone of formula IV.

Said last-named hydrazone, preferably in a watermiscible solvent such as a lower alkanol, is treated with cyanic or thiocyanic acid in the presence of an isonitrile of the formula $R^5NC$ such as a lower alkyl, cyclopentyl, or cyclohexyl isonitrile, to yield the corresponding imidazolidin-2-one or -2-thione of the formula I. This reaction is carried out at a temperature below room temperature, preferably within the range of from $-20°C$ to $20°C$. Moreover, it is advantageous to use aqueous solutions of alkali metal salts of cyanic or thiocyanic acid instead of the free acids, and to generate such acids from their respective alkali metal salts by addition of a mineral acid, preferably hydrochloric acid. The reaction is allowed to proceed for periods of time of from one hour to several days, whereupon a base, preferably ammonia, is added and the corresponding imidazolidin-2-one or -2-thione is isolated by filtration or by solvent extraction followed by evaporation of the solvent, and purified by crystallization.

Said last-named imidazolidin-2-ones or -2-thiones may be treated with a pharmacologically acceptable acid, for example, with hydrogen chloride in solution in a lower alkanol or in ether, to obtain the corresponding acid addition salt. Said last-named salts are pharmacologically equivalent to the compounds of formula I and may advantageously be used in their place.

In this manner, when using as starting materials e.g. N,N-dimethylhydrazine and n-butyraldehyde, isobutyraldehyde, or 2-phenylpropionaldehyde there are obtained the corresponding hydrazones, i.e. N,N-dimethyl-n-butyl, N,N-dimethylisobutyl, and N,N-dimethyl-2-phenypropyl hydrazone, respectively. When reacting said hydrazones with e.g. cyclohexylisonitrile and potassium cyanate or thiocyanate in the manner described above there are obtained 4-cyclohexylimino-1-dimethylamino-5-propylimidazolidin-2-one or -2-thione (I, $R^1 = R^2 = CH_3$, $R^3 = H$, $R^4 = CH_2CH_2CH_3$, $R^5 =$ cyclohexyl, $X = O$ or $S$), 4-cyclohexylimino-1-dimethylamino-5-isopropylimidazolidin-2-one or -2-thione (I, $R^1 = R^2 = CH_3$, $R^3 = H$, $R^4 = CH(CH_3)_2$, $R^5 =$ cyclohexyl, $X = O$ or $S$), and 4-cyclohexylimino-1-dimethylamino-5-($\alpha$-methylbenzyl)-imidazolidin-2-one or -2-thione (I, $R^1 = R^2 = CH_3$, $R^3 = H$, $R^4 = CH(CH_3)(C_6H_5)$, $R^5 =$ cyclohexyl, $X = O$ or $S$), respectively. When using as starting materials N-aminopiperidine, N-aminoazepine, or $N'$-amino-$N^4$-methylpiperazine and isobutyraldehyde or 2-phenylpropionaldehyde the hydrazones obtained are piperidinoisobutyl, azepinoisobutyl, and $N^4$-methylpiperazino-2-phenylpropyl hydrazone, which, after treatment with cyclohexylisonitrile and potassium cyanate or thiocyanate as above yield 4-cyclohexylimino-5-isopropyl-1-piperidino-imidazolidin-2-one or -2-thione, (I, $NR^1R^2 =$ piperidino, $R^3 = H$, $R^4 = CH(CH_3)_2$, $R^5 =$ cyclohexyl, $X = O$ or $S$), 1-azepino-4-cyclohexylimino-5-isopropylimidazolidin-2-one or -2-thione, (I, $NR^1R^2 =$ azepino, $R^3 = H$, $R^4 = CH(CH_3)_2$, $R^5 =$ cyclohexyl, $X = O$ or $S$), and 4-cyclohexylimino-1-(4'-methyl-1'-piperazino)-5-($\alpha$-methylbenzyl)imidazolidin-2-one and -2-thione, (I, $NR^1R^2 = 4'$-methyl-1'-piperazino, $R^3 = H$, $R^4 = CH(CH_3)(C_6H_5)$, $R^5 =$ cyclohexyl, $X = O$ or $S$), respectively.

It will be apparent to those skilled in the art that condensation of a substituted hydrazine of formula II with a cyclic ketone of the formula III in which $R^3$ and $R^4$ together with the carbonyl group are a carbocyclic ring yields the corresponding hydrazone of formula IV of said cyclic ketone.

Treatment of said hydrazone with an acid of the formula HCNX and an isonitrile of the formula $R^5NC$ in which X and $R^5$ are as defined in the first instance yields the corresponding compound of formula I which should be regarded as a derivative of an imidazolidin-2-one or 2-thione possessing a bivalent substituent in position 5 in the form of a carbocyclic ring attached in spiro fashion to carbon atom 5 of said imidazolidin-2-one or -2-thione. However, in accordance with the rules of nomenclature such compounds are designated in this Application as derivatives of 1,3-diazaspiro[4,4-]nonane or 1,3-diazaspiro[4,5]decane, depending upon the number of carbon atoms in the carbocyclic ring (5 or 6) attached in spiro fashion to carbon atom 5 of the imidazolidin-2-one or -2-thione nucleus.

In this manner, when using as starting materials e.g. N,N-dimethylhydrazine and cyclopentanone or cyclohexanone there are obtained N,N-dimethylcyclopentyl hydrazone and N,N-dimethylcyclohexyl hydrazone, respectively. Treatment of said hydrazones with e.g. cyclohexylisonitrile and potassium cyanate or thiocyanate yields 4-cyclohexylimino-1-dimethylamino-1,3-diazaspiro[4,4]nonan-2-one or -2-thione, (I, $R^1 = R^2 = CH_3$, $R^3 + R^4 = -(CH_2)_4-$, $R^5 =$ cyclohexyl, $X = O$ or S), and 4-cyclohexylimino-1-dimethylamino-1,3-diazaspiro[4,5]decan-2-one or -2-thione, (I, $R^1 = R^2 = CH_3$, $R^3 + R^4 = -(CH_2)_5-$, $R^5 =$ cyclohexyl, $X = O$ or S), respectively.

It should be noted, however, that it is not absolutely essential to prepare and isolate first the hydrazone of formula IV before condensing it with the appropriate isonitrile $R^5NC$ and cyanic or thiacyanic acid. In certain cases the hydrazine of formula II, the carbonyl compound of formula III, the isonitrile $R^5NC$ and an alkali metal cyanate or thiocyanate may be reacted together in solution in a lower alkanol in the presence of an acid at temperatures from 20°C to the reflux temperature of the mixture, to obtain, after working up in the manner described above, the corresponding imidazolidin-2-one or -2-thione.

The following Examples will illustrate this invention.

EXAMPLE 1

A mixture of N,N-dimethylhydrazine (21.0 g, 0.35 mole) and n-butyraldehyde (14.4 g, 0.2 mole) in anhydrous benzene (200 ml) is refluxed on the steam bath with continuous removal of water (Dean-Stark separator). When the reaction is complete the solvent is evaporated and the residue distilled, optionally under reduced pressure, to yield N,N-dimethyl-n-butyl hydrazone, b.p. 116°–122°c/15–17mm Hg.

In the same manner and using substantially the same molar proportions of reactants, but using the starting materials listed below, the following hydrazones are obtained.

| $R^1\!\!>\!\!N\!-\!NH_2(II)$ $R^2$ | $R^3COR^4(III)$ | Hydrazone(IV) | B.P., °C/mm Hg |
|---|---|---|---|
| N,N-Dimethyl-hydrazine | Isobutyraldehyde | N,N-Dimethylisobutyl | 118–125°/760 |
| N-Amino-piperidine | Isobutyraldehyde | Piperidinoisobutyl | 80–82°/15 |
| N-Amino-azepine | Isobutyraldehyde | Azepinoisobutyl | 92–98°/15–17 |
| N,N-Dimethyl-hydrazine | Cyclohexanone | N,N-Dimethylcyclo-hexyl | 177–180°/760 |
| N,N-Dimethyl-hydrazine | 2-Phenylpropion-aldehyde | N,N-Dimethyl-(α-methylphenethyl) | 108–116°/15–17 |

In the same manner, but using N,N-diethyl, N,N-dipropyl, 2-(5-nitrothiazolyl), or 2-(5-nitrofuryl)hydrazine, N-aminopiperazine, $N^4$-methyl-$N^1$-aminopiperazine, or N-aminomorpholine and treating with any of the above aldehydes or ketones the following hydrazones are also obtained:

N,N-diethyl-, N,N-dipropyl-, 2-(5-nitrothiazolyl)-, 2-(5-nitrofuryl)-, piperazino-, $N^4$-methylpiperazino-, or morpholino-n-butyl, isobutyl, cyclohexyl, and α-methylbenzyl hydrazone. In addition, when using the cyclopentanone or phenylacetaldehyde as the carbonyl compound, there are also obtained N,N-dimethyl-, N,N-diethyl-, N,N-dipropyl-, 2-(5-nitrothiazolyl)-, 2-(5-nitrofuryl)-, piperidino-, azepino-, piperazino-, $N^4$-methylpiperazino-, or morpholino-cyclopentyl or -benzyl hydrazones.

EXAMPLE 2

N,N-dimethyl-n-butyl hydrazone (11.4 g, 0.1 moles) is dissolved in methanol (150 ml), a solution of potassium cyanate (16.2 g, 0.2 moles) in water (30 ml) is added followed by cyclohexylisonitrile (10.9 g, 0.1 mole), the mixture is cooled in ice and hydrochloric acid (6N, 20 ml) is added dropwise with stirring. After 3 hours of stirring with cooling in ice ammonia (4N, 100 ml) is added, the mixture is extracted with methylene chloride, the extract washed with dilute ammonia and water, dried over anhydrous magnesium sulfate and evaporated under reduced pressure, to yield 4-cyclohexylimino-1-dimethylamino-5-propylimidazolidin-2-ones as an oil with $\nu_{max}^{Nujol}$ 3187, 3032, 1685 cm$^{-1}$. Treatment of said compound in solution in methanol with dry hydrogen chloride, with cooling, yields the corresponding hydrochloride salt with m.p. 140°–141°C after crystallization from methylene chloride-hexane.

In the same manner, using substantially the same molar proportions of reactants and substantially the same parameters of temperature and of reaction times the following compounds of formula I (substituted imidazolidin-2-ones and -2-thiones or substituted 1,3-diazaspiro[4,4]nonan-2-ones or -2-thiones or substituted 1,3-diazaspiro[4,5]decan-2-ones or -2-thiones) are obtained.

| Hydrazone (IV) | HCNX (Salt) | R⁵NC | Compounds of Formula I |
|---|---|---|---|
| N,N-Dimethyl-isobutyl | KCNO | Cyclohexyl-isonitrile | 4-Cyclohexylimino-1-dimethylamino-5-isopropylimidazolidin-2-one, m.p. 149–151.5°C, hydrochloride m.p. 162–163.5°C (methanol-acetone). |
| Piperidino-isobutyl | KCNO | Cyclohexyl-isonitrile | 4-Cyclohexylimino-5-isopropyl-1-piperidinoimidazolidin-2-one, m.p. 193–196°C, hydrochloride m.p. 201–203°C (methanol-acetone) |
| Azepino-isobutyl | KCNO | Cyclohexyl-isonitrile | 4-Cyclohexylimino-1-azepino-5-isopropylimidazolidin-2-one, $\nu_{max}^{Nujol}$ 3192, 3035, 1695cm⁻¹, hydrochloride m.p. 178–180°C(methylene-chloride-hexane). |
| N,N-Dimethyl-α-methylphenethyl | KCNO | Cyclohexyl-isonitrile | 4-Cyclohexylimino-1-dimethylamino-5-(α-methylbenzyl)-imidazolidin-2-one, $\nu_{max}^{Nujol}$ 3205, 3042, 1705 cm⁻¹, hydrochloride m.p. 157–158.5°C (methanol-isopropanol). |
| N,N-Dimethyl-cyclohexyl | KCNO | Cyclohexyl-isonitrile | 4-Cyclohexylimino-1-dimethylamino-1,3-diazaspiro[4,5]decan-2-one, m.p. 282–284°C(methanol). |
| N,N-Dimethyl-cyclohexyl | KCNS | Cyclohexyl-isonitrile | 4-Cyclohexylimino-1-dimethylamino-1,3-diazaspiro[4,5]decane-2-thione, m.p. 247–249°C (methanol). |

In the same manner, but using as starting materials the N,N-diethyl, N,N-dipropyl, 2-(5-nitrothiazolyl), 2-(5-nitrofuryl), piperazino, N⁴-methylpiperazino, or morpholino analogs of the hydrazones listed above together with potassium cyanate and cyclohexyl isonitrile, the corresponding 1-diethylamino, 1-dipropylamino, 1-[2-(5-nitrothiazolyl)], 1-[2-(5-nitrofuryl)], 1-piperazino, 1-(N⁴-methylpiperazino), and 1-morpholino analogs of the compounds of formula I listed above are also obtained.

In the same manner, but using as starting material any of the cyclopentyl or benzyl hydrazones described in Example 1, together with potassium cyanate and cyclohexylisonitrile, there are obtained the correspondingly substituted 1,3-diazaspiro[4,4]nonan-2-ones and the correspondingly substituted 5-benzylimidazolidin-2-ones of formula I.

In the same manner, but using as starting materials any of the hydrazones listed above together with cyclopentylisonitrile, methyl, ethyl, or t-butyl isonitrile and potassium cyanate, the 4-cyclopentylimino, 4-methylimino, 4-ethylimino, and 4-t-butylimino analogs of the compounds of formula I described above are obtained.

In the same manner, using as starting materials any of the hydrazones listed above together with any of the isonitriles listed above and potassium thiocyanate, there are obtained the 2-thione analogs of the imidazolidin-2ones, 1,3-diazaspiro[4,4]nonan-2-ones, and 1,3-diazaspiro[4,5]decan-2-ones listed above.

EXAMPLE 3

A solution of N¹-amino-N⁴-methylpiperazine (0.1 mole), 2-phenylpropionaldehyde (0.1 mole), and cyclohexylisonitrile (0.1 mole) in methanol (125 ml) is mixed with potassium cyanate (0.2 moles) dissolved in water (30 ml). Hydrochloric acid (6N, 20 ml) is added dropwise with stirring at room temperature, and the mixture is stirred at room temperature for 2 days, adding occasionally a few drops of hydrochloric acid so as to keep it acidic. Ammonia (4N, 100 ml) is added, the mixture is extracted with methylene chloride, the extracts washed with dilute ammonium hydroxide and water, dried over anhydrous magnesium sulfate, and evaporated under reduced pressure, to yield 4-cyclohexylimino 1-(4'-methyl-1'-piperazino)-5-(α-methylbenzyl)imidazolidin-2-one, m.p. 197°–203°C. Treatment of said last-named compound with hydrogen chloride in ether solution yields the corresponding hydrochloride salt, m.p. 236°–238°C (methanole-thanol).

In the same manner, but using potassium thiocyanate instead of potassium cyanate, the corresponding 4-cyclohexylimino-1-(4'-methyl-1'-piperazino)-5-(α-methylbenzyl)-imidazolidin-2-thione is also obtained.

Again in the same manner, but using n-butyraldehyde, isobutyraldehyde, phenylacetaldehyde, cyclopentanone, or cyclohexanone instead of 2-phenylpropionaldehyde, potassium cyanate or potassium thiocyanate, and cyclopentyl, methyl, ethyl, or t-butyl isonitrile instead of cyclohexylisonitrile, there are obtained the 4-cyclopentylimino, 4-methylimino, 4-ethylimino, and 4-t-butylimino derivatives of 5-propyl-, 5-isopropyl-, or 5-benzyl-1-(4'-methyl-1'-piperazino)imidazolidin-2-ones -2-thiones, and of 1-(4'-methyl-1'-piperazino)-1,3-diazaspiro[4,4]nonan-2-one and -2-thione, and of 1-(4'-methyl-1'-piperazino-1,3-idazaspiro[4,5]decan-2-one and -2-thione.

In the same manner, as above, any of the free bases listed in Examples 2 or 3 may be treated with solutions of sulfuric, acetic, maleic, or citric acid to obtain the corresponding sulfate, acetate, maleate, or citrate salts.

We claim:
1. A compound selected from those of the formula

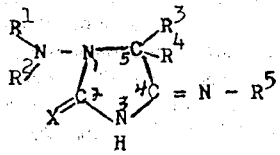

in which $R^1$ and $R^2$ together with the nitrogen atom to which they are attached form an azepino ring; $R^3$ is selected from the group which consists of hydrogen and lower alkyl; $R^4$ is lower alkyl; $R^5$ is selected from the group which consists of cycloalkyl having 5-6 carbon atoms; X is selected from the group which consists of oxygen and sulfur; or acid addition salts thereof with pharmacologically acceptable acids.

2. The hydrochloric salt of 4-cyclohexylimino-5-isopropyl-1-piperidinoimidazolidin-2-one, as claimed in Claim 1.

3. 4-Cyclohexylimino-1-azepino-5-isopropylimidazolidin-2-one, as claimed in Claim 1.

4. The hydrochloride salt of 4-cyclohexylimino-1-azepino-5-isopropylimidazolidin-2-one, as claimed in Claim 1.

* * * * *